US009163853B2

(12) United States Patent
Fujiwara

(10) Patent No.: US 9,163,853 B2
(45) Date of Patent: Oct. 20, 2015

(54) NOISE CONTROL SYSTEM, AND FAN STRUCTURE AND OUTDOOR UNIT OF AIR-CONDITIONING-APPARATUS EACH EQUIPPED THEREWITH

(75) Inventor: Susumu Fujiwara, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 816 days.

(21) Appl. No.: 13/504,006

(22) PCT Filed: Nov. 2, 2009

(86) PCT No.: PCT/JP2009/068752

§ 371 (c)(1),
(2), (4) Date: Apr. 25, 2012

(87) PCT Pub. No.: WO2011/052088

PCT Pub. Date: May 5, 2011

(65) Prior Publication Data

US 2012/0210741 A1 Aug. 23, 2012

(51) Int. Cl.

| | |
|---|---|
| ***A61F 11/06*** | (2006.01) |
| ***G10K 11/16*** | (2006.01) |
| ***H03B 29/00*** | (2006.01) |
| ***F24F 13/24*** | (2006.01) |
| ***F24F 1/06*** | (2011.01) |

(Continued)

(52) U.S. Cl.
CPC . *F24F 13/24* (2013.01); *F24F 1/06* (2013.01); *F24F 1/40* (2013.01); *G10K 11/1786* (2013.01); *F24F 2013/247* (2013.01); *G10K 2210/12* (2013.01)

(58) Field of Classification Search
CPC ..... G10K 11/178; G10K 11/002; H04R 3/002
USPC .............................. 381/71.2, 71.3, 71.7, 71.8
See application file for complete search history.

(56) References Cited

U.S. PATENT DOCUMENTS 3,940,575 A * 2/1976 Bauer ........................... 381/177
4,329,547 A 5/1982 Imai (Continued)

FOREIGN PATENT DOCUMENTS

JP 55-120300 A 9/1980
JP 1-147235 A 6/1989

(Continued)

OTHER PUBLICATIONS

International Search Report (PCT/ISA/210) issued on Mar. 2, 2010, by Japanese Patent Office as the International Searching Authority for International Application No. PCT/JP2009/068752.

(Continued)

*Primary Examiner* — Alexander Jamal
(74) *Attorney, Agent, or Firm* — Buchanan Ingersoll & Rooney PC

(57) ABSTRACT

To provide a noise control system capable of generating a noise cancellation field where noise is reduced at a desired position in a space. An error scanning filter generates a noise cancellation signal using an adaptive control algorithm based on error scanning, the signal having a phase opposite to that of an acoustic signal component detected by a reference sensor. A control speaker radiates the noise cancellation signal to create a noise cancellation field near the head of a person receiving sound.

12 Claims, 7 Drawing Sheets

(51) Int. Cl.
*F24F 1/40* (2011.01)
*G10K 11/178* (2006.01)

(56) References Cited

U.S. PATENT DOCUMENTS

| | | | | | |
|---|---|---|---|---|---|
| 4,614,090 | A * | 9/1986 | Kaneko et al. | 62/158 |
| 4,947,434 | A * | 8/1990 | Ito | 381/71.7 |
| 5,125,241 | A * | 6/1992 | Nakanishi et al. | 62/296 |
| 5,343,713 | A * | 9/1994 | Okabe et al. | 62/296 |
| 5,689,572 | A * | 11/1997 | Ohki et al. | 381/71.3 |
| 2003/0165395 | A1* | 9/2003 | Sekiya et al. | 420/434 |
| 2006/0285697 | A1* | 12/2006 | Nishikawa et al. | 381/71.1 |
| 2010/0119098 | A1* | 5/2010 | Heil | 381/368 |
| 2012/0164931 | A1* | 6/2012 | Takeda et al. | 454/239 |

FOREIGN PATENT DOCUMENTS

| | | | |
|---|---|---|---|
| JP | 5-112726 | A | 5/1993 |
| JP | 6-102886 | A | 4/1994 |
| JP | 6-138883 | A | 5/1994 |
| JP | 6-348282 | A | 12/1994 |
| JP | 8-63174 | A | 3/1996 |
| JP | 8-140807 | A | 6/1996 |
| JP | 9-106290 | A | 4/1997 |
| JP | 9-106291 | A | 4/1997 |
| JP | 11-141966 | A | 5/1999 |
| JP | 2006-197283 | A | 7/2006 |
| JP | 2007-089814 | A | 4/2007 |
| JP | 2007-163025 | A | 6/2007 |

OTHER PUBLICATIONS

Office Action (Notice of Reasons for Rejection) issued on Sep. 10, 2013, by the Japanese Patent Office in corresponding Japanese Patent Application No. 2011-538201, and an English Translation of the Office Action. (7 pages).

Japanese Office Action for corresponding Japanese Appln. No. 2011-538201 dated Jan. 21, 2014, with English-language translation (2 pages).

* cited by examiner

NOISE CONTROL SYSTEM, AND FAN STRUCTURE AND OUTDOOR UNIT OF AIR-CONDITIONING-APPARATUS EACH EQUIPPED THEREWITH

TECHNICAL FIELD

The present invention relates to a noise control system employing active noise control in an open space to create a noise cancellation field in a desired space, and a fan structure and an outdoor unit of an air-conditioning apparatus that are equipped with the system.

BACKGROUND ART

Examples of anti-noise measures applying adaptive signal processing have been reported and means for creating a noise cancellation field in an ambient environment of a sleeping person has been reported.

For example, noise cancellation pillows that creates a noise cancellation field while a person is sleeping have been proposed, in which an active noise control system, which creates a noise cancellation field around the person receiving noise while his/her sleep, is configured in the pillow (for example, refer to Patent Literature 1 and Patent Literature 2).

CITATION LIST

Patent Literature

Patent Literature 1: Japanese Unexamined Patent Application Publication No. 8-140807

Patent Literature 2: Japanese Unexamined Patent Application Publication No. 2007-89814

SUMMARY OF INVENTION

Technical Problem

In such a system configuration, a sensor for picking up noise and a secondary noise source for noise cancellation need to be mounted on the pillow. Disadvantageously, depending on where the person receiving the sound moves his or her head position to, the head may cover the secondary noise source, not allowing the noise cancellation signal necessary for the noise cancellation to be generated, for example.

The present invention has been made to overcome the above-described disadvantage and an object of the present invention is to provide a noise control system capable of creating a noise cancellation field, where noise is reduced, at a desired position in a space.

Solution to Problem

A noise control system according to the present invention includes: one or more reference sensors that picks up a noise source signal from a noise source; one or more control speakers that radiates a noise cancellation signal for canceling the noise source signal; two or more error sensors arranged in a field subject to noise cancellation (hereinafter, referred to as a "noise cancellation field") by the noise cancellation signal, the error sensors picking up an acoustic signal in the noise cancellation field (hereinafter, referred to as an "acoustic signal of the noise cancellation field"); and an error scanning filter that generates the noise cancellation signal by employing adaptive signal processing based on an adaptive control algorithm from the noise source signal picked up by the reference sensors and from the acoustic signal of the noise cancellation field picked up by the error sensors, in which the noise cancellation signal radiated from the control speakers generates the noise cancellation field in a predetermined space area.

ADVANTAGEOUS EFFECTS OF INVENTION

According to the noise control system of the invention, one or more reference sensors, one or more control speakers, and two or more error sensors are arranged to enable creation of a noise cancellation field at an intended position in a space where noise is to be reduced, thus forming a comfortable space.

DESCRIPTION OF EMBODIMENT

Embodiment 1

(Configuration of Noise Control System)

Figure 1:
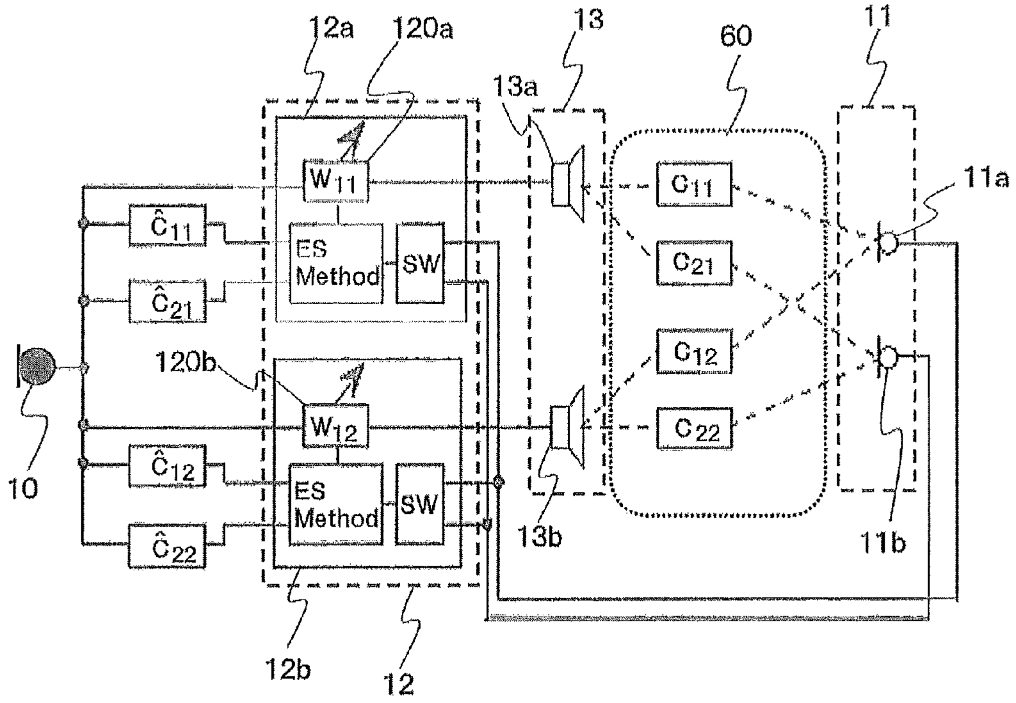
FIG. 1 is a diagram illustrating a configuration of a noise control system according to Embodiment 1 of the invention.

FIG. 1 is a diagram illustrating a configuration of a noise control system according to Embodiment 1 of the invention. The configuration of the noise control system will be described below with reference to FIG. 1.

The noise control system according to Embodiment 1 of the invention includes at least a reference sensor 10, error sensors 11, error scanning filters 12, and control speakers 13.

The reference sensor 10 is a sensor that detects a noise source signal of a noise and includes, for example, a microphone.

Although as the reference sensor 10, only one channel is depicted in FIG. 1, the invention is not limited to this case. A plurality of channels may be arranged.

Furthermore, although the reference sensor 10 includes a microphone as described above, the invention is not limited to this case. The sensor may include detecting means, such as a vibration and acceleration pickup for picking up vibration.

Each of the error sensors 11 is a sensor that receives a signal after the noise cancellation has been performed to the noise source signal by effect of a cancellation signal generated by the control speakers, which will be described later, and includes, for example, a microphone. As illustrated in FIG. 1, a first error sensor 11*a* and a second error sensor 11*b* are arranged as the error sensors 11.

Although in FIG. 1, the first error sensor 11*a* and the second error sensor 11*b*, namely, the two error sensors 11 are illustrated, the invention is not limited to this case. The system may be configured such that one or more than three error sensors 11 may be arranged.

Furthermore, although each of the error sensors 11 includes a microphone as described above, the invention is not limited to this case. The sensor may include detecting means, such as a vibration and acceleration pickup for picking up vibration.

Each of the error scanning filters 12 is a filter for performing coefficient variation using the filtered-X LMS algorithm for adaptive signal processing. As shown in FIG. 1, a first error scanning filter 12*a* and a second error scanning filter 12*b* are arranged as the error scanning filters 12. The first error scanning filter 12*a* is connected to the above-described first and second error sensors 11*a* and 11*b*. The second error scanning filter 12*b* is similarly connected to the first and second error sensors 11*a* and 11*b*. In addition, the first error scanning filter 12*a* and the second error scanning filter 12*b* include a first filter characteristic stage 120*a* and a second filter characteristic stage 120*b*, respectively, each stage serving as a filter characteristic stage for generating a noise cancellation signal. The first filter characteristic stage 120*a* and the second filter characteristic stage 120*b* are connected to the reference sensor 10.

Although in FIG. 1 the first error scanning filter 12*a* and the second error scanning filter 12*b*, namely, the two error scanning filters 12 are illustrated, the invention is not limited to this case. The system may be configured such that one or more than three error scanning filters 12 may be arranged.

Each of the control speakers 13 is a secondary noise source for noise cancellation used to generate a noise cancellation signal generated by the first filter characteristic stage 120*a* or the second filter characteristic stage 120*b* and has, for example, a speaker structure. As shown in FIG. 1, a first control speaker 13*a* and a second control speaker 13*b* are arranged as the control speakers 13. The first control speaker 13*a* is connected to the first filter characteristic stage 120*a* in the first error scanning filter 12*a*. Furthermore, the second control speaker 13*b* is connected to the second filter characteristic stage 120*b* in the second error scanning filter 12*b*.

Although the control speakers 13 each have a speaker structure as described above, the invention is not limited to this case. The speakers may each have a vibrating structure that causes vibration.

Although in FIG. 1 the first control speaker 13*a* and the second control speaker 13*b*, namely, the two control speakers 13 are illustrated, the invention is not limited to this case. The system may be configured such that one or more than three control speakers 13 may arranged.

(Operation of Noise Control System)

An adaptive control algorithm based on error scanning for performing noise control in the noise control system according to Embodiment 1 will now be described with reference to FIG. 1.

The space between the error sensors 11 and the control speakers 13 is an unpredictable sound field and a noise cancellation field 60 to be created by the noise control system according to Embodiment is created in this unpredictable sound field. The error sensors 11 are used to monitor the environmental change in the condition of the sound field of the noise cancellation field 60. Furthermore, since the noise cancellation field 60 is created between the error sensors 11 and the control speakers 13, it is dependent of the installation positions of the error sensors 11 and the control speakers 13, and can be created at an intended position in the sound field.

Each of the error sensors 11 inputs the acoustic signal component associated with the sound radiation of the control speaker 13, and propagation characteristics based on a transfer function of the propagation path from the speaker 13 to the error sensor 11 is measured. Attention will now be drawn to the first error sensor 11*a*, serving as one of the error sensors 11. The first error sensor 11 a inputs an acoustic signal component from the first control speaker 13*a*, thus measuring a transfer function C11 of the propagation path from the first error sensor 11*a* to the first control speaker 13*a* in the noise cancellation field 60. In addition, the first error sensor 11*a* inputs an acoustic signal component from the second control speaker 13*b*, thus measuring a transfer function C12 of the propagation path from the first error sensor 11*a* to the second control speaker 13*b* in the noise cancellation field 60.

Attention will now be drawn to the second error sensor 11*b*. The second error sensor 11*b* inputs an acoustic signal component from the first control speaker 13*a*, thus measuring a transfer function C21 of the propagation path from the second error sensor 11*b* to the first control speaker 13*a* in the noise cancellation field 60. In addition, the second error sensor 11*b* inputs an acoustic signal component from the second control speaker 13*b*, thus measuring a transfer function C22 of a propagation path from the second error sensor 11*b* to the second control speaker 13*b* in the noise cancellation field 60.

Performing the above-described operation at all times enables confirmation of, for example, a noise source signal propagating in the noise cancellation field 60, variation factors of the noise cancellation field 60, and the characteristics of devices that require control (in this case, the reference sensor 10, the error sensors 11, and the control speakers 13). Accordingly, stable noise cancellation characteristics can be obtained.

Furthermore, since there is a period of time during which the devices are stopped in order to perform scanning, the number of devices may be increased. Accordingly, the noise cancellation field 60 can be enlarged.

Prior to the execution of noise control, an arbitrary signal is radiated from the control speakers at arbitrary time intervals, and with the detection of the signal by the reference sensor 10 and the error sensors 11, transfer functions can be measured. Thus, the installation positions of the reference sensor 10 and the error sensors 11, the number of sensors 10 installed, and the number of sensors 11 installed can be confirmed. Transfer characteristics based on the measured transfer functions are transmitted through the reference sensor 10 and the error sensors 11 to the error scanning filters 12 for producing noise cancellation signals.

During the execution of noise control, the input signals to the error sensors 11 are the signal components of the noise cancellation field 60, which is the space subject to noise canceling, and therefore, the signal components need to be as close to nil as possible. The input signals function in the error scanning filters 12 as a basic signal of the noise cancellation field 60, which is the space in which noise has been canceled. Here, each error scanning filter 12 performs calculation based on the least squares method in order to cancel the signal component that need to be canceled, and performs an operation of producing a signal shape necessary for the noise cancellation field 60 on the basis of the result of the calculation. The reference sensor 10 receives the noise source signal. The error scanning filters 12 each performs convolution integration of this signal component and generates a cancellation signal of the opposite phase. This noise cancellation signal of the opposite phase is transmitted from the first filter characteristic stage 120*a* (or the second filter characteristic stage 120*b*) to the corresponding control speaker 13. The control speaker 13 generates and radiates the noise cancellation signal.

Each error scanning filter 12 receives a signal component detected by the error sensors 11, compares phase characteristics of the signal component with those of the noise cancellation signal radiated from the control speakers 13 to confirm an external signal other than the noise source signal, namely, an environment change factor that changes the noise cancellation field 60, and generates a new noise cancellation signal on the basis of a signal component opposite in phase to the signal component detected by the error sensors 11. This noise cancellation signal is transmitted to the corresponding control speaker 13 and is then radiated from the control speaker 13 in order to cancel noise from a noise source. A basic action necessary for noise cancellation in the noise cancellation field 60 is performed by the above-described operation. The above-described "signal component detected by the error sensors 11" correspond to an "acoustic signal of the noise cancellation field" in the invention.

(Configuration and Operation of Noise Control System When Applied to Vicinity of Head of Person Receiving Sound)

Figure 2:
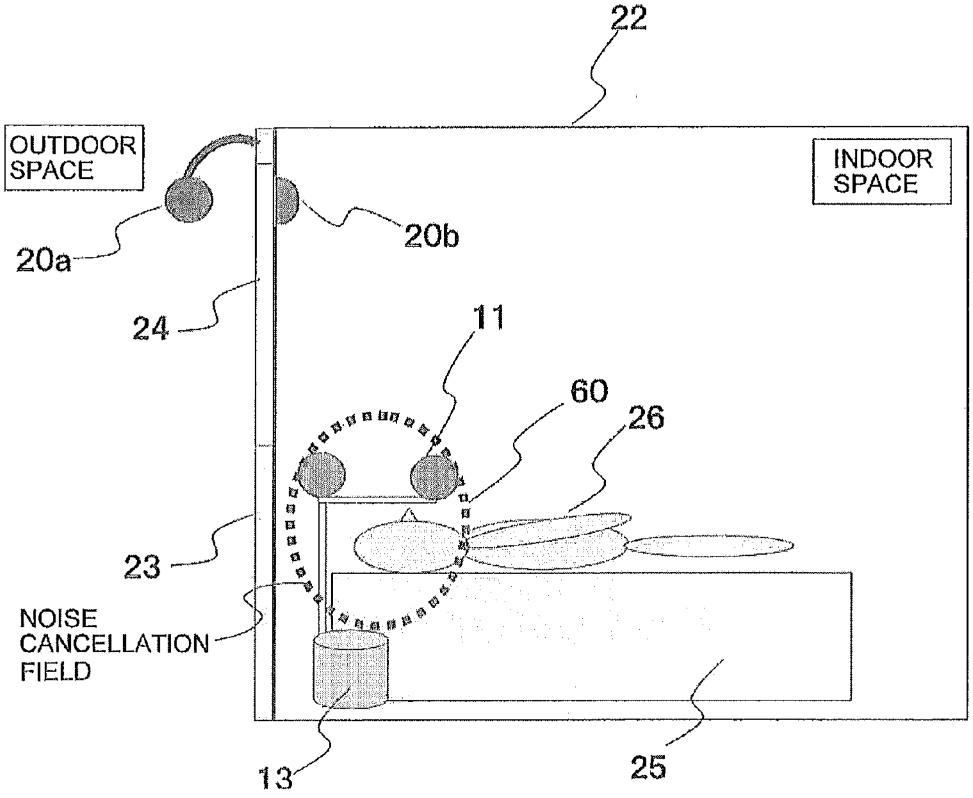
FIG. 2 is a side view of the noise control system according to Embodiment 1 of the invention in the case where the system is disposed in the vicinity of the head of a person receiving sound.
Figure 3:
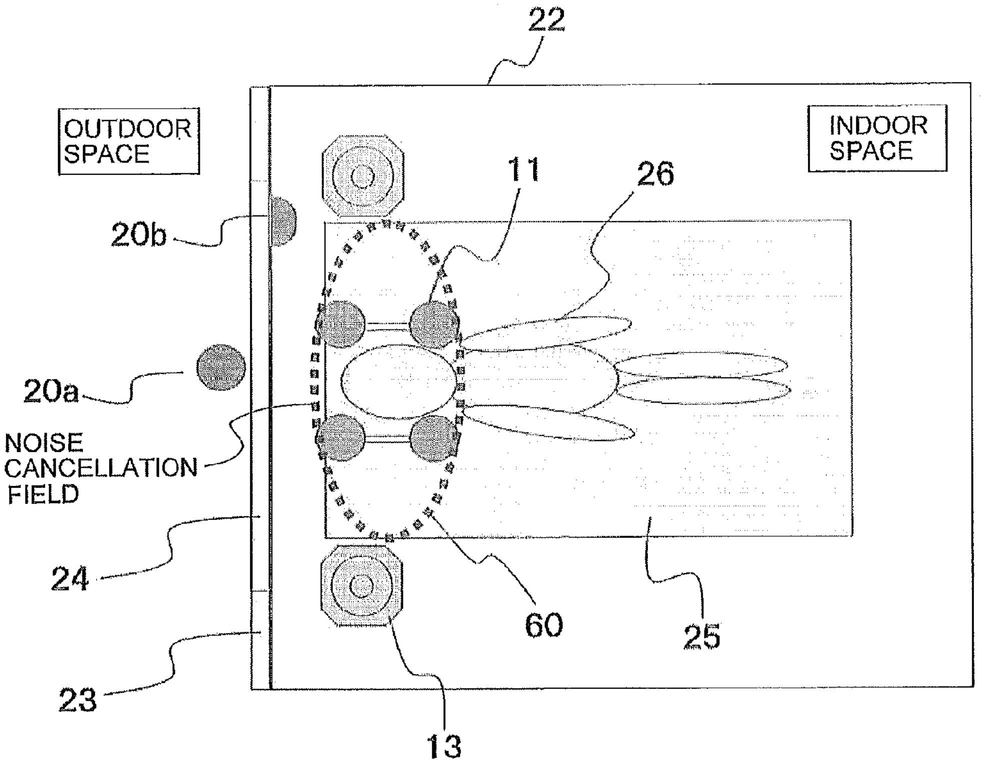
FIG. 3 is a top view of the noise control system according to Embodiment 1 of the invention in the case where the system is disposed in the vicinity of the head of the person receiving sound.

FIG. 2 is a side view of the noise control system according to Embodiment 1 of the invention in the case where the system is disposed in the vicinity of the head of a person receiving sound, and FIG. 3 is a top view thereof.

Referring to FIGS. 2 and 3, a piece of bedding furniture 25, such as a bed, is disposed in a housing (building) 22 and a person 26 receiving sound is lying down on the bedding furniture 25. A wall 23, which is a part of the housing 22, includes a glass plate 24 disposed at an arbitrary position. An outdoor reference sensor 20*a* is fixed directly or through a jig or the like to the outer surface of the wall 23. In addition, an indoor reference sensor 20*b* is attached to the inner surface of the wall 23. Furthermore, two control speakers 13, each arranged on each side of the bedding furniture where the head of the person receiving sound is positioned when the person is lying down, which is, specifically, a position corresponding to both ears. In addition, four error sensors 11 are arranged above the head of the sound receiving person 26 so as to surround the head.

Note that the above-described outdoor and indoor reference sensors 20*a* and 20*b* correspond to the reference sensor 10 in FIG. 1.

It should be noted that the arrangement of the components illustrated in FIGS. 2 and 3 is an exemplary arrangement. The invention is not limited to this arrangement. For example, the number of error sensors 11 or control speakers 13 and the arrangement thereof may differ.

Furthermore, although in FIGS. 2 and 3 the single outdoor reference sensor 20*a* and the single indoor reference sensor 20*b*, namely, a total of two reference sensors are illustrated, the invention is not limited to this case. The system may be configured such that one or more reference sensors 20*a* and one or more reference sensors 20*b* may be arranged.

Figure 4:
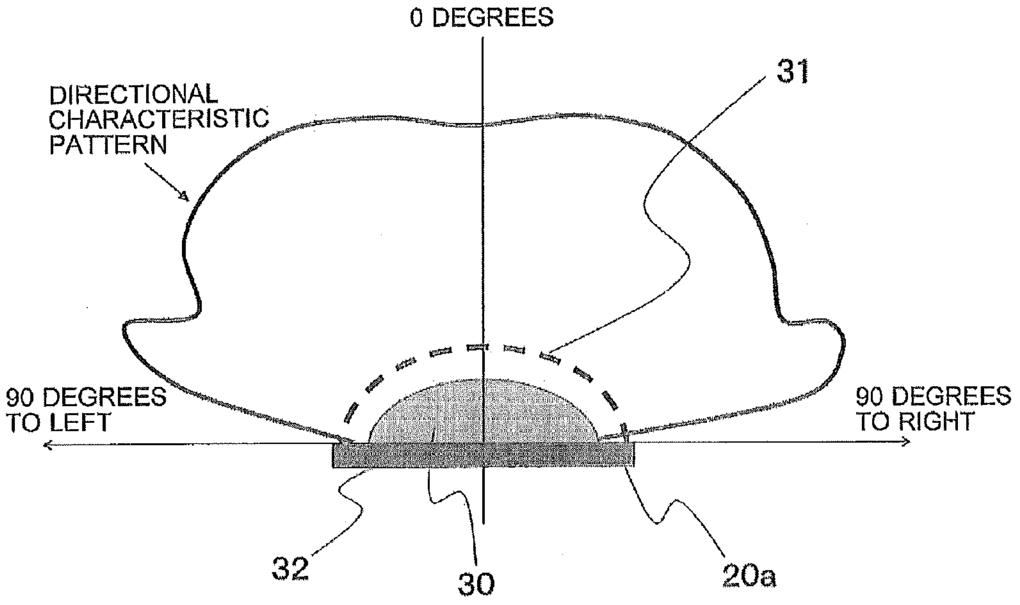
FIG. 4 is a diagram illustrating a schematic structure and directional characteristics of an outdoor reference sensor 20*a* that is employed when the noise control system according to Embodiment 1 of the invention is disposed in the vicinity of the head of the person receiving sound.

FIG. 4 is a diagram illustrating a schematic structure and directional characteristics of an outdoor reference sensor 20*a* that is employed when the noise control system according to Embodiment 1 of the invention is disposed in the vicinity of the head of the person receiving sound.

As shown in FIG. 4, the outdoor reference sensor 20*a* includes at least a dome-shaped sound receiving plate 30, serving as a sound receiving portion, a waterproof windshield 31 fixed on the front side of the dome-shaped sound receiving plate 30, and a sensor housing 32, serving as a housing of the outdoor reference sensor 20*a*.

With the outdoor reference sensor 20*a* having a microphone structure, the outdoor reference sensor 20*a* can receive the acoustic signal component propagating through a space with the entire surface of its dome-shaped sound receiving plate 30, as illustrated by the directional characteristics in FIG. 4. Moreover, the directional characteristics illustrated in FIG. 4 indicates that, conversely, this microphone structure cannot receive an acoustic signal component propagating from the rear side of its dome-shaped sound receiving plate 30.

The sensor housing 32 is constituted by a material capable of transforming vibrational energy of a vibrational component at or below 300 Hz into thermal energy to remove vibration, for example, a polymer damping material, such as mica or isinglass, or silicon.

The dome-shaped sound receiving plate 30 is disposed such that its back thereof is against the housing 22, namely, the rear surface of the sensor housing 32 of the outdoor reference sensor 20*b* faces the wall 23. Accordingly, the dome-shaped sound receiving plate 30 can reliably detect the outdoor acoustic signal component generated outdoors that is propagating toward the wall 23 and penetrating into an indoor space.

In this case, as regards the outdoor noise, an acoustic signal of 300 HZ or lower has a long wavelength and high acoustic energy. Accordingly, the wall 23 or the glass plate 24 is vibrated, and the signal propagates as vibrational sound. Since this vibrational sound directly vibrates the housing 22, the sound propagates through the sensor housing 32 of the outdoor reference sensor 20*a* and vibrates the sensor housing 32. However, a vibrational sound component different from the acoustic signal component generated by air vibration propagating to the dome-shaped sound receiving plate 30 of the outdoor reference sensor 20*a* are also detected, thus causing phase distortion in the detected signal. In some cases, disadvantageously, an acoustic signal detected by the dome-shaped sound receiving plate 30 is canceled. However, the damping material constituting the sensor housing 32 can serve as a measure against such a problem. As described above, the outdoor reference sensor 20*a* is disposed at an arbitrary position on the housing 22 and detects the acoustic signal component propagating from the outdoor space to the housing 22.

However, a large portion of the acoustic signal in the noise generated outdoors penetrate the glass plate 24 disposed at an arbitrary position in the wall 23 of the housing 22 and enter the indoor space. Sound that enters through the glass plate 24 vibrates the glass plate 24, thus causing vibrational sound. In addition to the vibrational sound that vibrates the wall 23 of the housing 22 and enters the indoor space, resonance is generated affected by the inner dimensions of the housing 22, thus causing resonance sound having a very low frequency component. The indoor reference sensor 20*b* picks up all of the above-described propagated and vibrational sound of the penetration, and resonance sound generated in the indoor space. Furthermore, the indoor reference sensor 20*b* has similar directional characteristics to that of the outdoor reference sensor 20*a*. Unlike the sensor housing 32 of the outdoor reference sensor 20*a*, it is not constituted by a material having excellent damping capacity, but is constituted by resin or metal that has high resistance to aging deterioration and is excellent in terms of quality so as to be capable of detecting vibrational sound propagating through the wall 23. In other words, the indoor reference sensor 20*b* is disposed on or near the glass plate 24, or on the wall 23, which tends to propagate outdoor noise, and functions as a detector that detects the acoustic signal components in the housing 22, which defines the indoor space.

As described above, the outdoor reference sensor 20*a* is disposed at an arbitrary position on the outdoor side of the wall 23 of the housing 22 and the indoor reference sensor 20*b* is disposed at an arbitrary position on the wall 23 of the housing 22 such that the sensors detect the acoustic signal component intended to be canceled. The acoustic signal component in the noise detected by the outdoor reference sensor 20*a* and the indoor reference sensor 20*b* are transmitted to the error scanning filters 12 (not illustrated in FIGS. 2 and 3) of the noise control system according to Embodiment 1. The error scanning filters 12 generate noise cancellation signals having a phase opposite to that of the acoustic signal component detected by the reference sensors, using the foregoing adaptive control algorithm based on error scanning. Then, the control speakers 13 radiate the generated noise cancellation signals to create a noise cancellation field 60 near the head of the sound receiving person 26.

Figure 5:
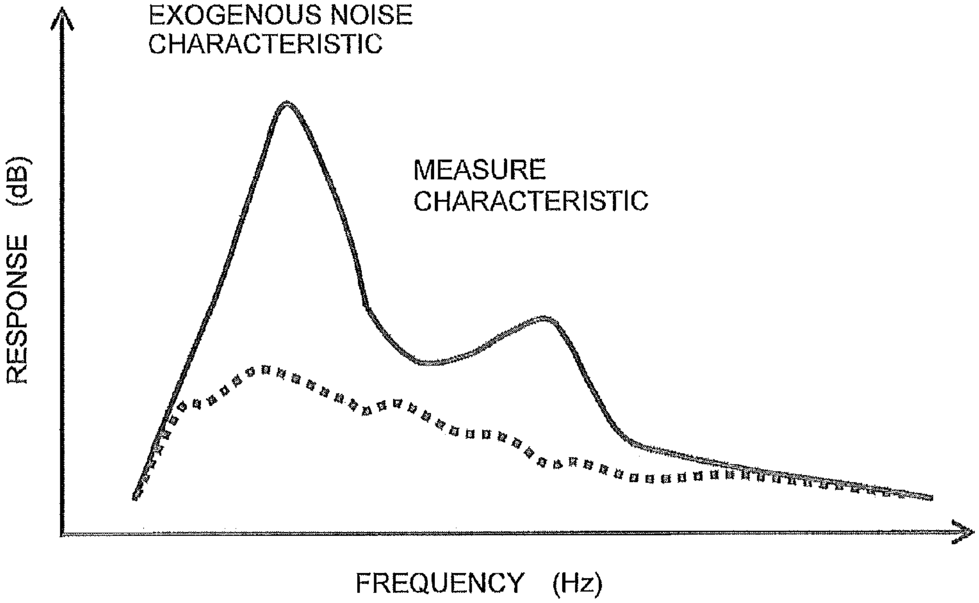
FIG. 5 is a graph illustrating the comparison of a frequency characteristic of a noise cancellation field 60 created in the vicinity of a person 26 receiving sound with a frequency characteristic of noise generated indoors and outdoors in the noise control system according to Embodiment 1 of the invention.

FIG. 5 is a graph illustrating the comparison between a frequency characteristic (hereinafter, referred to as a "measure characteristic") in the noise cancellation field 60 created near the sound receiving person 26 in the noise control system according to Embodiment 1 of the invention and a frequency characteristic of noise (hereinafter, referred to as an "exogenous noise characteristic") created in the indoor space and the outdoor space.

FIG. 5 indicates that a sound pressure level in the problematic low frequency band is reduced by up to 20 dB or more in the noise cancellation field 60.

[Advantageous Effects of Embodiment 1]

As described above with respect to the configuration and operation, noise cancellation signals radiated from the control speakers 13 enable generation of the noise cancellation field 60 where noise is reduced in the desired space, and thus a comfortable space can be provided.

Furthermore, in the related art, a typical system is configured such that a sensor for detecting noise is disposed near a pillow. Accordingly, a noise signal from a noise source generated indoors can be picked up, but external noise propagating from an outdoor space to the indoor space is not received by the sensor for picking up noise disposed in the indoor space. Disadvantageously, it is therefore not possible to detect the signal component of the noise propagating from the outdoor space to the indoor space and perform a noise cancellation operation for noise reduction. Moreover, as regards a propagation path from the outdoor space to the indoor space, the path often exists in the window glass. A sensor of the related art disposed near a person receiving sound cannot detect a noise signal that has passed through the window glass, and therefore only sound generated near the person receiving sound in the indoor space is detected and canceled. According to Embodiment 1, while, for example, the sound receiving person 26 is sleeping in the bedding furniture 25, a noise cancellation field 60 is created in the vicinity of the head of the sound receiving person 26, in which the noise cancellation field 60 suppresses the acoustic signal component of the noise generated outdoors, the vibrational sound component that enter the indoor space from the outdoor space, resonance sound generated in the indoor space, and the like using noise cancellation signals.

In the related art, in the case where a secondary noise source for noise cancellation is disposed in, for example, a pillow, the size of the sound source has to be inevitably small and thin. Disadvantageously, no measure can be taken against, for example, infrasonic noise generated by low frequency noise at or below 300 Hz. According to Embodiment 1, the noise cancellation field 60 can be created without using a specially designed pillow or the like, thus providing a comfortable sleeping environment which is not disturbed by noise and in which low frequency noise can be reduced.

While Embodiment 1 has been described with respect to the case where the noise control system illustrated in FIG. 1 is applied so as to reduce indoor noise as illustrated in FIGS. 2 and 3, the invention is not limited to this case. The invention is applicable to a consumer, business, or industrial product or the like which requires noise control.

Furthermore, while Embodiment has been described with respect to the case where the noise cancellation field 60 is created in the vicinity of the head of the sound receiving person 26, the invention is not limited to this case. It is needless to say that the region may be created at other desired positions.

Embodiment 2

A fan structure 40, which will be described later, equipped with a noise control system according to Embodiment 2 is equipped with the same noise control system that is illustrated in FIG. 1 in Embodiment 1.

(Configuration of Fan Structure 40 with Noise Control System)

Figure 6:
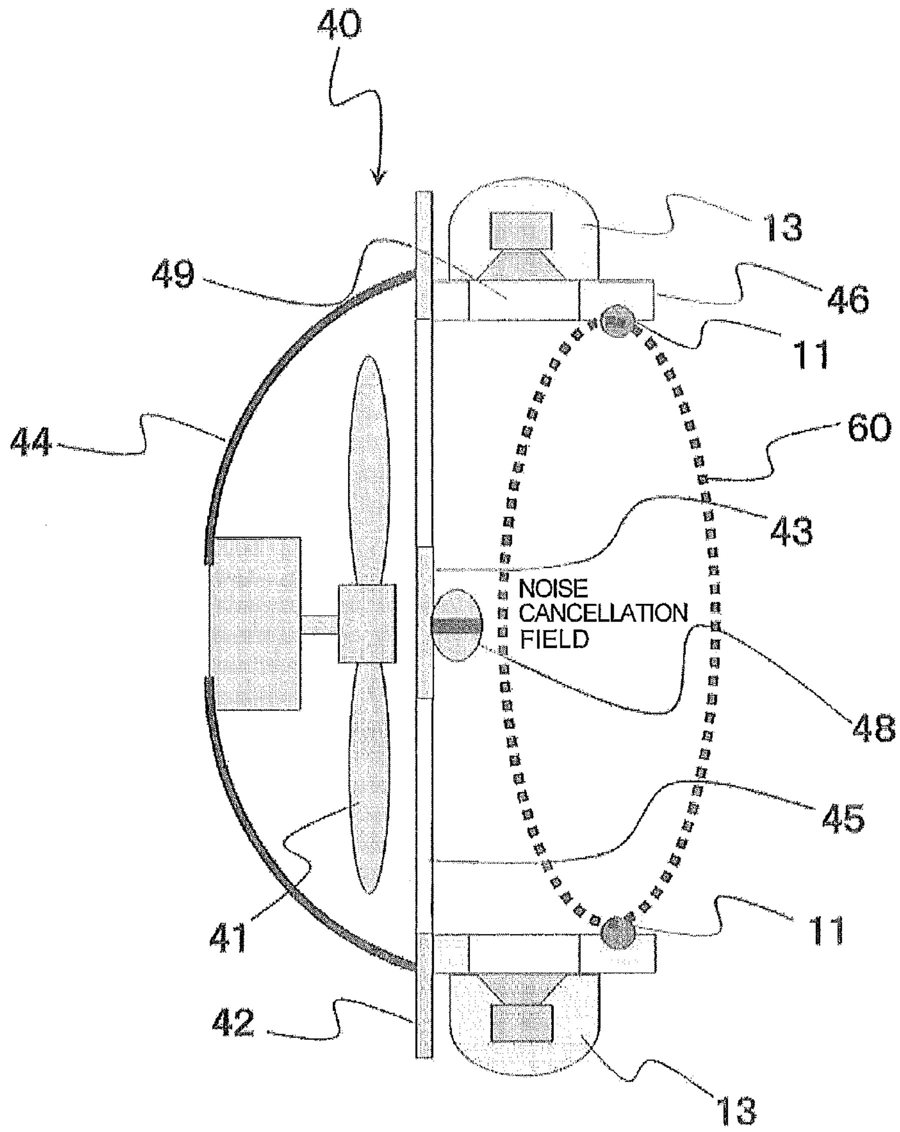
FIG. 6 is a side view of a fan structure 40 equipped with a noise control system according to Embodiment 2 of the invention.
Figure 7:
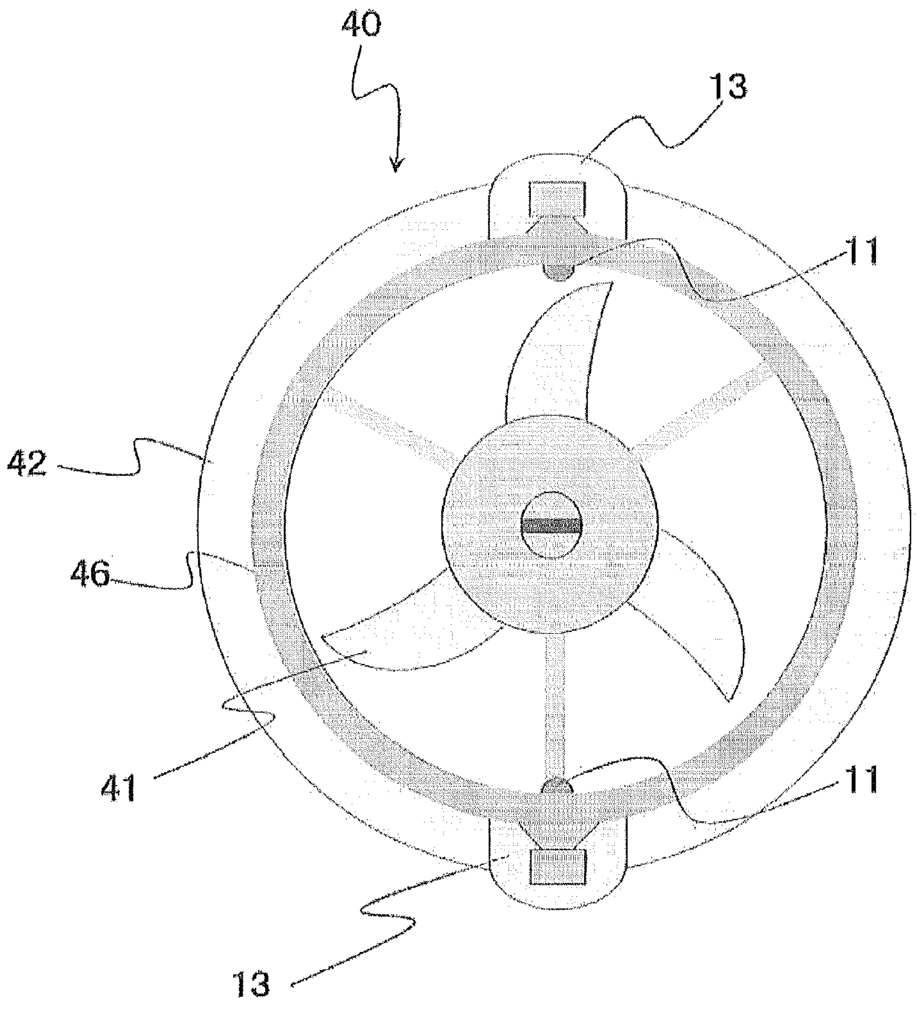
FIG. 7 is a front view of the structure of the fan structure 40 equipped with the noise control system according to Embodiment 2 of the invention.

FIG. 6 is a side view of a structure of the fan structure 40 equipped with the noise control system according to Embodiment 2 of the invention. FIG. 7 is a front view thereof.

As shown in FIGS. 6 and 7, the fan structure 40, such as a ventilation fan, includes at least a fan member 41 including a plurality of blades, a fan guide 42 disposed in front of the fan member 41, a baffle plate 43, attached to the fan guide 42, the baffle plate 43 having arbitrary dimensions, a bowl-shaped attachment jig fixed to the fan guide 42 such that the fan member 41 is fixed to the center of the jig, an opening 45 for intake or exhaust, the opening 45 serving as an opening of the fan guide 42, and a doughnut-shaped passage guide 46 having an arbitrary depth, the doughnut-shaped passage guide 46 attached to an outer rim of the fan guide 42.

Note that the above-described fan guide 42 and attachment jig 44 correspond to a "housing" of the invention and the passage guide 46 corresponds to a "guide member" of the invention.

The baffle plate 43 is provided with a reference sensor 48 disposed at substantially the center thereof. This reference sensor 48 is constituted by two outdoor reference sensors 20*a* in Embodiment 1 such that the sensor housings 32 of the sensors are fixed together. The reference sensor 48 can therefore be used as a microphone having a 360-degree directional characteristic.

The passage guide 46 has sound openings 49 arranged at arbitrary positions. As illustrated in FIG. 6, the sound openings 49 are arranged at two positions in the circular passage guide 46 so as to face each other. Control speakers 13 are arranged on the outer surface of the passage guide 46 corresponding to the positions where the sound openings 49 are each located. In addition, error sensors 11 are each arranged on the inner surface of the passage guide 46 near the sound openings 49. The error sensors 11 are attached to the passage guide 46 such that more than half of each sensor is embedded in the guide in order not to interfere with the passage and in order to prevent causing turbulent sound in the passage. Furthermore, the passage guide 46 is constituted by resin or metal having high vibration damping efficiency in order to prevent the flow of fluid taken in and exhausted by the fan member 41 from being disturbed to cause turbulent flow and in order not to hinder exhaust and intake performance. In addition, the depth of the passage guide 46 is set to be substantially the same as the sum of the diameter of a diaphragm of the control speaker 13 and an outer dimension of the error sensor 11 or slightly larger than the sum. This can prevent the generation of turbulent flow and fluid sound in the passage guide 46, which is generated when guiding length of the passage guide 46 is increased.

Furthermore, in order to reduce generation of fluid sound as described above, a sound absorbing material may be fixed to the inner surface of the passage guide 46.

Furthermore, while in FIG. 6 the fan structure is configured such that the passage guide 46 has two sound openings 49, the invention is not limited to this case. One or more than three sound openings may be arranged. In this case, the control speaker 13 and the error sensor 11 may be arranged for each sound opening 49 such that these components are positioned as described above.

(Operation of Fan Structure 40 Equipped with Noise Control System)

Figure 8:
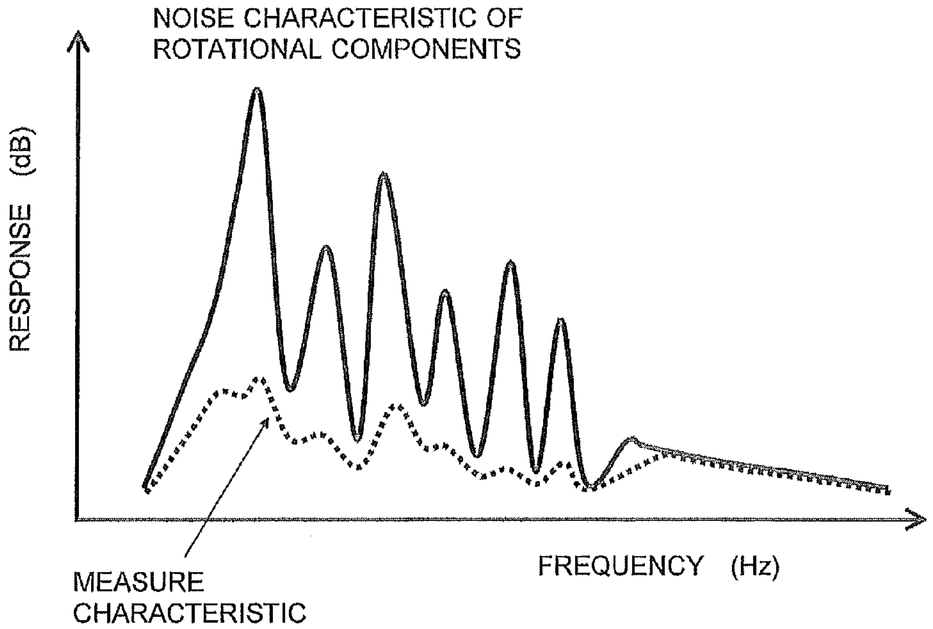
FIG. 8 is a graph illustrating the comparison of a frequency characteristic of a noise cancellation field 60 with a frequency characteristic of noise associated with rotation of a fan member 41 in the fan structure 40 equipped with the noise control system according to Embodiment 2 of the invention.

FIG. 8 is a graph illustrating the comparison between a frequency characteristic (measure characteristic) in a noise cancellation field 60 and a frequency characteristic of the noise associated with rotation of the fan member 41 (hereinafter, referred to as a "noise characteristic of the rotational component) in the fan structure 40 equipped with the noise control system according to Embodiment 2 of the invention.

In the fan structure 40, accompanying the rotation of the fan member 41, noise is generated with the noise characteristic of the rotational component, which has peak frequencies as illustrated in FIG. 8. As regards the peak frequency, assuming the frequency of the rotational component of the fan member 41 (f=N (rotation speed)/60) as a reference, by multiplying the blade number Z to this frequency accompanying the rotation, a peak frequency of an order component (fn=N/60*Z) is obtained, in which the peak frequency of the order component occurs at high levels. The frequency f of the rotational component of the fan member 41 varies depending on the size and application of the fan structure 40. In some cases, low frequency component at or below 100 Hz occur. In some cases, the peak frequency fn, which is the product of the frequency f of the rotational component and the number of blades Z, occurs up to around 1 kHz, thus causing uncomfortable noise containing a frequency component ranging from a low band to a middle band. At this time, the reference sensor 48 is disposed on the opposite side of the baffle plate 43 to the fan member 41 and detects the peak frequency of the rotational component that occurs in the fan member 41. Furthermore, the reference sensor 48 is made to have a 360-degree directional characteristic because, during rotation of the fan member 41, the relationship of the shape of the fan member 41 and a rotating state thereof with a propagation path of the peak frequency component in the space are not clearly known. With this arrangement, the peak frequency component can be reliably detected irrespective of the shape and the rotating state of the fan member 41. The peak frequency component detected by the reference sensor 48 is transmitted to the error scanning filters 12 (not illustrated in FIGS. 6 and 7). The error scanning filters 12 generate noise cancellation signals having a phase opposite to that of the peak frequency component using the adaptive control algorithm based on error scanning described in Embodiment 1. Then, the control speakers 13 radiate the generated noise cancellation signals to the inside of the passage guide 46, thus creating a noise cancellation field 60 inside the passage guide 46. Specifically, the passage guide 46 functions as a noise cancellation area for creating the noise cancellation field 60. Since noise containing the peak frequency component generated in the fan member 41 is inevitably radiated to the inside of the passage guide 46, the noise containing the peak frequency component is canceled in the passage guide 46. The structure of this passage guide 46 permits the acoustic signal of the noise containing the peak frequency component to be canceled inside the passage guide 46 prior to being three-dimensionally radiated from the passage guide 46. Fluid component, subject to noise cancellation, passes through the passage guide 46 and is radiated three-dimensionally. With the above-described operation, as shown in FIG. 8, in the noise cancellation field 60, each peak frequency of the noise characteristic of the rotational component is attenuated to a sound pressure level similar to a base level shown in the measure characteristics.

[Advantageous Effects of Embodiment 2]

As described above with respect to the configuration and operation, the fan structure 40, such as a ventilation fan, can be obtained which can suppress the acoustic signal component of the noise accompanying the rotation of the fan member 41 using noise cancellation signals and can prevent noise from being radiated from the passage guide 46.

Embodiment 3

An air-conditioning apparatus 50, which will be described later, equipped with a noise control system according to Embodiment 3 is equipped with the same noise control system that is illustrated in FIG. 1 in Embodiment 1.

(Configuration of Outdoor Unit 50 with Noise Control System)

Figure 9:
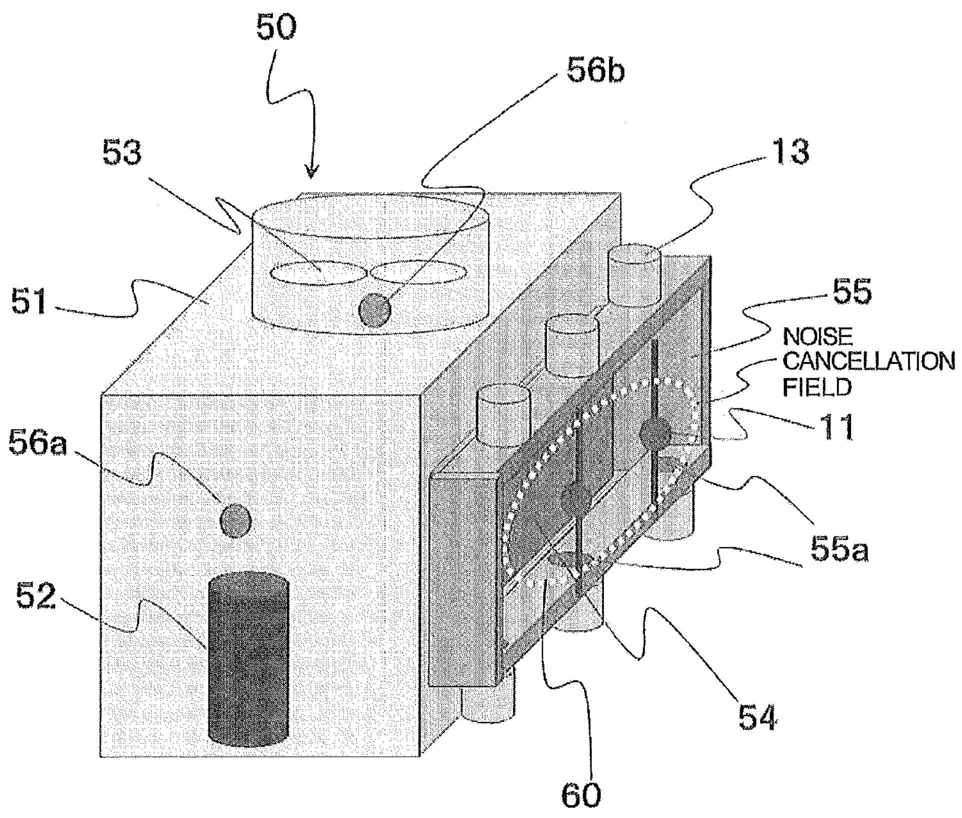
FIG. 9 is a perspective view of a structure of an outdoor unit 50 of an air-conditioning apparatus in which the outdoor unit is equipped with a noise control system according to Embodiment 3 of the invention.

FIG. 9 is a perspective view of a structure of an outdoor unit 50 of an air-conditioning apparatus in which the outdoor unit is equipped with a noise control system according to Embodiment 3 of the invention.

As shown in FIG. 9, the outdoor unit 50 of the air-conditioning apparatus includes at least an outdoor-unit housing 51 defining the outer shape of the outdoor unit 50, one or more compressors 52 disposed in the outdoor-unit housing 51, an intake fan 53 for taking air into the outdoor-unit housing 51, a heat exchanger member 54 disposed on at least one surface of the outdoor-unit housing 51, and a frame-shaped exhaust sound guide 55, disposed on an outer end of the heat exchanger member 54, having an arbitrary depth.

Furthermore, the above-described outdoor-unit housing 51 corresponds to the "housing" of the invention and the exhaust sound guide 55 corresponds to the "guide member" of the invention.

The exhaust sound guide 55 has six sound openings **55*a* arranged at arbitrary positions. Control speakers 13 are arranged on the circumference surfaces of the exhaust sound guide 55 corresponding to the positions where the sound openings 55*a* are located. In addition, two error sensors 11 are arranged at arbitrary positions in an outermost portion of the exhaust sound guide 55. Furthermore, the depth of the exhaust sound guide 55 is substantially the same as the diameter of the diaphragm of each control speaker 13. This can prevent the exhaust sound guide 55 from becoming a second noise source, in which the noise is generated when the member constituting the exhaust sound guide 55 vibrates due to the increase in the depth of the exhaust sound guide 55. Furthermore, although the exhaust sound guide 55 also functions as an outlet of the heat exchanger member 54, even when the depth is elongated, the exhaust sound guide 55** is capable of preventing the heat radiation to be hindered, that is, is capable of preventing the drop of heat exchange efficiency.

Furthermore, in order to reduce the noise that has been generated as above, a sound absorbing material may be fixed to the inner surfaces of the exhaust sound guide 55.

Although in FIG. 9 six sound openings 55*a* are arranged in the exhaust sound guide 55, the invention is not limited to this case. The number of sound openings 55*a* arranged may be other than six and, in this case, it is only necessary to dispose a control speaker 13 for each sound opening 55*a*.

Furthermore, although in FIG. 9 two error sensors 11 are arranged at positions in an outermost portion of the exhaust sound guide 55, the invention is not limited to this case. One or more than three error sensors may be arranged.

In addition, a compressor reference sensor 56*a* is disposed near the compressor 52 and detects vibrational sound associated with the rotating motion of the compressor 52. Furthermore, a fan reference sensor 56*b* is disposed near the intake fan 53 and detects fluid sound of a fan member.

Furthermore, although in FIG. 9 the single compressor reference sensor 56*a* and the single fan reference sensor 56*b* are arranged, the invention is not limited to this case. A plurality of compressor reference sensors 56*a* and a plurality of fan reference sensors 56*b* may be arranged.

(Operation of Outdoor Unit 50 with Noise Control System)

In the outdoor unit 50, outside air taken in through the intake fan 53 is subject to heat exchange in the heat exchanger member 54 and is then discharged to the outside through the exhaust sound guide 55. At this time, noise associated with rotation of the compressor 52 and noise associated with rotation of the intake fan 53 are three-dimensionally radiated to the outside via a path of the outside air, which passes through the heat exchanger member 54 and the exhaust sound guide 55.

Although FIG. 9 illustrates the configuration in which a single compressor 52 is disposed, the invention is not limited to this case. A plurality of compressors may be arranged. This compressor 52 is subject to rotation speed control by an inverter (not illustrated). At this time, for example, it is assumed that two compressors 52 are arranged and the compressors are controlled by corresponding inverters such that the rotation speed is set to, for example, 1200 rotations per unit time. In this case, vibrational sound having a frequency f=N (rotation speed)/60 is generated associated with the rotation. At this time, since the rotation speed of the compressor is N=1200 (rotations per unit time), vibrational sound of 60 Hz is generated. Although the two compressors 52 are controlled at 1200 rotations per unit time by each inverter, for example, affected by the bearing condition (sliding, abrasion, or the like) of each compressor 52 or the difference in temperature rise of cooling oil between main bodies of the compressors 52, a slight difference in rotation speed between the compressors may occur. This difference creates a difference of about 1 Hz to 2 Hz in vibrational sound frequency between the compressors 52. The difference in frequency causes a phenomenon called "beat note". In the case where a plurality of compressors 52 are arranged in FIG. 9, therefore, noise associated with rotation of the compressors 52, noise associated with rotation of the intake fan 53, and the above-described "beat note" are three-dimensionally radiated to the outside through the heat exchanger member 54 and the exhaust sound guide 55.

The noise and "beat note" associated with rotation of the compressors 52 are detected by the compressor reference sensor 56*a* and the noise associated with rotation of the intake fan 53 is detected by the fan reference sensor 56*b*. The detected noises are transmitted to the error scanning filters 12 (not illustrated in FIG. 9). The error scanning filters 12 generate noise cancellation signals having a phase opposite to that of the peak frequency component using the adaptive control algorithm based on error scanning described in Embodiment 1. Then, the control speakers 13 radiate the generated noise cancellation signals to the inside of the exhaust sound guide 55, thus creating a noise cancellation field 60 inside the exhaust sound guide 55. Specifically, the exhaust sound guide 55 functions as a noise cancellation area for creating the noise cancellation field 60. Since noise generated in the compressors 52 and the fan member 41 is inevitably radiated to the inside of the exhaust sound guide 55, the noise is canceled in the exhaust sound guide 55. The structure of the exhaust sound guide 55 permits an acoustic signal of the noise to be canceled inside the exhaust sound guide 55 prior to being three-dimensionally radiated from the passage guide 55. Fluid component, subject to noise cancellation, passes through the passage guide 55 and is radiated three-dimensionally.

Figure 10:
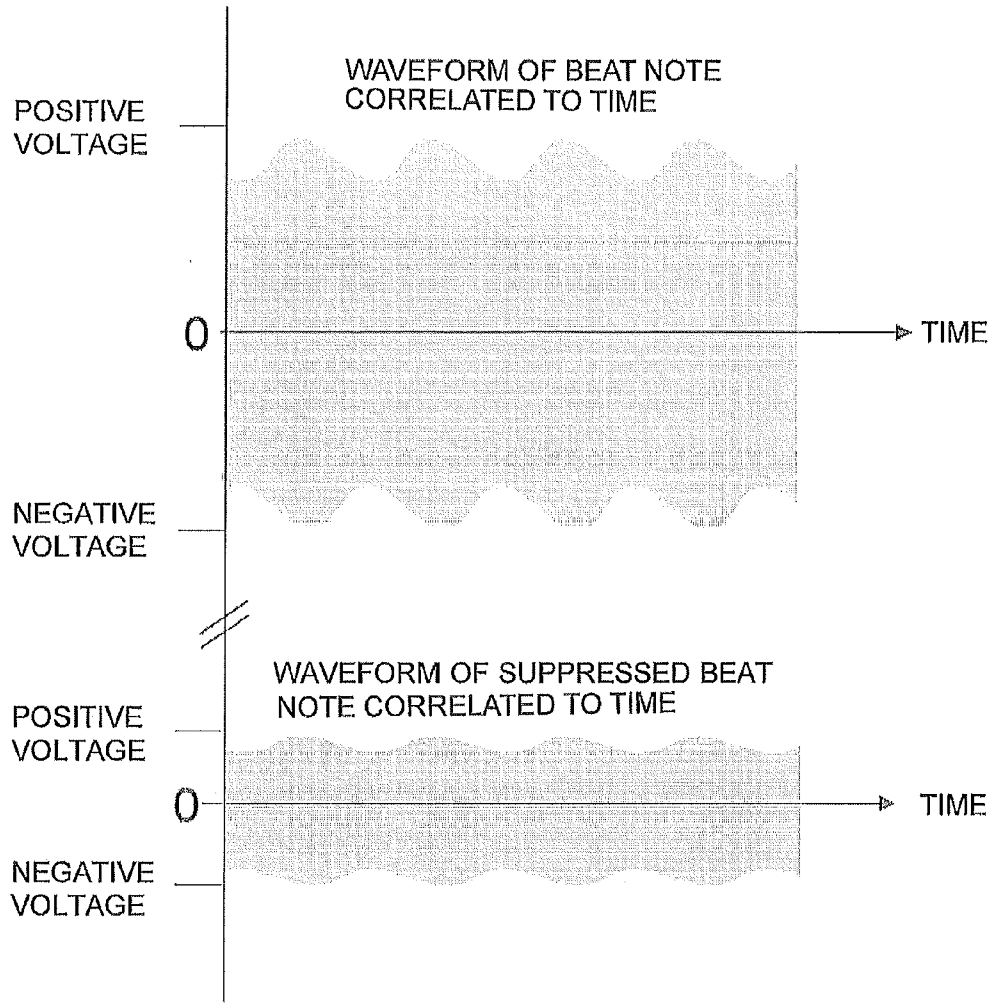
FIG. 10 is a diagram illustrating a noise reduction effect of beat note in the outdoor unit 50 of the air-conditioning apparatus in which the outdoor unit is equipped with the noise control system according to Embodiment 3 of the invention.

FIG. 10 is a diagram illustrating a noise reduction effect of beat note in the outdoor unit 50 of the air-conditioning apparatus in which the outdoor unit is equipped with the noise control system according to Embodiment 3 of the invention.

The waveform in the upper diagram of FIG. 10 indicates variation of the noise correlated with time at positions of the error sensors 11 while beat note is generated from a plurality of compressors. A large fluctuation is observed as a waveform. On the other hand, the waveform in the lower diagram of FIG. 10 indicates variation of the noise correlated with time at positions of the error sensors 11 while the noise is suppressed by the noise cancellation signal of the noise control system according to Embodiment 3. The waveform indicates that fluctuations are attenuated as compared with the upper waveform.

[Advantageous Effects of Embodiment 3]

As described above with respect to the configuration and operation, the outdoor unit 50 of the air-conditioning apparatus can be obtained which can suppress noise or beat note associated with rotation of the compressors 52 and the acoustic signal component of noise associated with rotation of the intake fan 53 using noise cancellation signals and can prevent noise from being radiated from the exhaust sound guide 55.

Reference Signs List

10 reference sensor; 11 error sensor; 11*a* first error sensor; 11*b* second error sensor; 12 error scanning filter; 12*a* first error scanning filter; 12*b* second error scanning filter; 13 control speaker; 13*a* first control speaker; 13*b* second control speaker; 20*a* outdoor reference sensor; 20*b* indoor reference sensor; 22 housing; 23 wall; 24 glass plate; 25 bedding furniture; 26 sound receiving person; 30 dome-shaped sound receiving plate; 32 sensor housing; 40 fan structure; 41 fan member; 42 fan guide; 43 baffle plate; 44 attachment jig; 45 opening; 46 passage guide; 48 reference sensor; 49 sound opening; 50 outdoor unit; 51 outdoor-unit housing; 52 compressor; 53 intake fan; 54 heat exchanger member; 55 exhaust sound guide; 56*a* compressor reference sensor; 56*b* fan reference sensor; 60 noise cancellation field; 120*a* first filter characteristic stage; and 120*b* second filter characteristic stage.

The invention claimed is:

1. An outdoor unit of an air-conditioning apparatus comprising:

a housing having an intake opening for intake;

a compressor disposed inside the housing;

an intake fan that takes air from the intake opening into the housinq;

a passage guide provided on an outer end of the intake opening;

a heat exchanger that is accommodated in the housing and exchanges heat with the air taken in from the intake opening by the intake fan;

one or more reference sensors arranged adjacent to the intake fan in the passage guide, the reference sensors picking up a noise source signal from the intake fan;

one or more control speakers that are attached onto the passage guide and radiate a noise cancellation signal for canceling the noise source signal to generate a noise cancellation field in the passage guide;

one or more error sensors arranged in the noise cancellation field, the error sensors picking up an acoustic signal in the noise cancellation field; and an error scanning filter that generates the noise cancellation signal by employing adaptive signal processing based on an adaptive control algorithm from the noise source signal picked up by the reference sensors and from the acoustic signal of the noise cancellation field picked up by the error sensors.

2. The outdoor unit of the air-conditioning apparatus of claim 1, wherein the error sensors are arranged inside the passage guide and near the control speakers.

3. The outdoor unit of the air-conditioning apparatus of claim 1, wherein a guiding depth of the passage guide is the same or larger than the sum of the diameter of a diaphragm of the control speaker and an outer dimension of the error sensor.

4. The outdoor unit of the air-conditioning apparatus of claim 1, wherein the passage guide is constituted by resin or metal, having high vibration damping efficiency.

5. The outdoor unit of the air-conditioning apparatus of claim 1, wherein a sound absorbing material is fixed to the inner surface of the passage guide.

6. An outdoor unit of an air-conditioning apparatus, comprising:

a housing having an exhaust opening for exhaust;

a compressor disposed inside the housing;

an intake fan that takes air into the housing;

a heat exchanger acommodated in the housing, the heat exchanger exchanges heat with the air taken in by the intake fan;

an exhaust sound guide that is disposed on an outer end of the exhaust opening;

two or more reference sensors arranged adjacent to the intake fan and the compressor, and collect a noise source signal from the compressor and the intake fan;

one or more control speakers that are attached onto the exhaust sound guide, and radiate a noise cancellation signal for canceling the noise source signal to generate a noise cancellation field in the exhaust sound guide;

one or more error sensors arranged in the noise cancellation field and pick up an acoustic signal in the noise cancellation field; and an error scanning filter that generates the noise cancellation signal by employing adaptive signal processing based on an adaptive control algorithm from the noise source signal picked up by the reference sensors and from the acoustic signal of the noise cancellation field picked up by the error sensors.

7. The outdoor unit of the air-conditioning apparatus of claim 6, wherein the error sensors are arranged in an outermost portion of the exhaust sound guide.

8. The outdoor unit of the air-conditioning apparatus of claim 6, wherein the guiding depth of the exhaust sound guide is the same as the diameter of a diaphragm of the control speaker.

9. The outdoor unit of the air-conditioning apparatus of claim 6, wherein the compressor is one of two or more compressors arranged, and when a slight difference in rotation speed between the two or more compressors causes beat noise, the control speakers reduce the beat noise using the output noise cancellation signal.

10. The outdoor unit of the air-conditioning apparatus of claim 6, wherein each of the reference sensors includes a dome-shaped sound receiving plate, and picks up the noise source signal through the sound receiving plate from all areas.

11. The outdoor unit of the air-conditioning apparatus of claim 1, wherein a sensor housing of the reference sensor is constituted by a polymer damping material having a damping capacity or a material such as silicon.

12. The outdoor unit of the air-conditioning apparatus of claim 1, wherein the reference sensor is disposed at the center of the intake fan and has a 360-degree directional characteristic.

* * * * *